United States Patent [19]

Inada et al.

[11] Patent Number: 4,814,098

[45] Date of Patent: Mar. 21, 1989

[54] MAGNETIC MATERIAL-PHYSIOLOGICALLY ACTIVE SUBSTANCE CONJUGATE

[75] Inventors: Yuji Inada, Tokyo; Yutaka Tamaura, Yokohama; Katsunobu Takahashi, Tokyo, all of Japan

[73] Assignee: Bellex Corporation, Tokyo, Japan

[21] Appl. No.: 90,505

[22] Filed: Aug. 28, 1987

[30] Foreign Application Priority Data

Sep. 6, 1986 [JP] Japan ................................ 61-209982
Oct. 23, 1986 [JP] Japan ................................ 61-252479

[51] Int. Cl.$^4$ ...................... C04B 35/00; C04B 35/26
[52] U.S. Cl. ............................... 252/62.51; 252/62.53; 252/62.54; 252/62.56; 252/62.57; 128/653; 128/654; 424/1.1; 424/2; 424/3; 210/695
[58] Field of Search ................. 128/653, 654; 424/1.1, 424/2, 3; 210/695; 252/62.53, 62.54, 62.51

[56] References Cited

U.S. PATENT DOCUMENTS

| | | | |
|---|---|---|---|
| 3,474,777 | 10/1969 | Figge et al. | 604/36 |
| 4,101,435 | 7/1978 | Hasegawa et al. | 252/62.54 |
| 4,169,804 | 10/1979 | Yapel, Jr. | 252/62.54 |
| 4,331,654 | 5/1982 | Morris | 252/62.53 |
| 4,335,094 | 1/1982 | Mosbach | 424/1 |
| 4,413,070 | 11/1983 | Renbaum | 252/62.54 |
| 4,554,088 | 11/1985 | Whitehead et al. | 252/62.54 |
| 4,642,447 | 3/1987 | Gries et al. | 128/654 |
| 4,645,741 | 2/1987 | Inada . | |
| 4,952,773 | 6/1984 | Molday | 252/62.54 |

OTHER PUBLICATIONS

Hawley, *Condensed Chemical Dictionary*, 10th Ed., Van Nostrand Reinhold, N.Y., 1981, pp. 831–832.
Biochemical and Biophysical Research Communications, vol. 142, No. 2, Jan. 30, 1987, pp. 291–296.
Biochemical and Biophysical Research Communications, vol. 145, No. 2, Jun. 15, 1987, pp. 908–914.
Biotechnology Letters, vol. 8, No. 12, Dec. 1986, pp. 877–880.

*Primary Examiner*—William R. Dixon, Jr.
*Assistant Examiner*—David M. Brunsman
*Attorney, Agent, or Firm*—Frishauf, Holtz, Goodman & Woodard

[57] ABSTRACT

Disclosed is a conjugate comprising a magnetic material and a physiologically active substance bound to each other through a polyethylene glycol derivative, and a conjugate comprising a magnetic material and a polyethylene glycol derivative bound to each other. According to the present invention, a bioreactor enabling application to or recovery of physiologically active substances under liquid state by utilizing the magnetic properties is provided.

24 Claims, No Drawings

MAGNETIC MATERIAL-PHYSIOLOGICALLY ACTIVE SUBSTANCE CONJUGATE

BACKGROUND OF THE INVENTION

This invention relates to a conjugate (M-P-E) formed by binding a magnetic material (M) and a physioloqically active substance (E) to each other through a polyethylene glycol derivative (P) which is an amphiphatic substance for both of water and organic solvents, having physiological activity stably dispersed or dissolved as colloid in both of aqueous solutions and organic solvents, and to a bioreactor enabling application to or rocovery of physiologically active substances the liquid state by utilizing the magnetic properties.

For example, enzymes have been generally dealt with as bioreactors in aquieous solutions, and if their physiological activites can be exerted in organic solvents and utilized for organic syntheses and the like, application range and possibility of biotechnology can be greatly broadened. In short, if enzymes can be catalytic efficiency therein, they can become utilized for more reactions such as reverse reactions of hydrolysis or enzymatic treatment of hydrophobic substances only slightly soluble in water. Furtherwise, other proteins than enzymes can be solubilized in organic solvents and the functions of the proteins can be exhibited in organic solvents. Accordingly, the present inventor has made it possible to solubilize enzymes in orqanic solvents by modification with amphiphatic polymers (Japanese Unexamined Patent Publication No. 156395/1985). However, for utilizing generally physiologically active substances, recovery and reutilization of these are required. As the method for recovery of enzyme proteins, in place of the method in which enzyme proteins are insolubilized by binding with a polymeric or inorganic material carrier and recovered by sedimentation or centrifugation, magnetic separation enabling rapid and simple separation is recently attracting attention. Among these methods, there may be included the method in which proteins are directly adsorbed on the surfaces of magnetic material particles, the method in which the magnetic material particle surfaces are adsorbed or coated with an organic polymer (polyacrylamide, dextran, starch, bovine serum albumin, cellulose) and proteins are then bound thereto, and electromagnets in general can separate magnetic materials with particle sizes to about 30 nm, and superconductive electromagnets can separate those with further smaller sizes. However, these conjugates (M-E) can be dispersed only in aqueous solutions, but agglomerated in organic solvents to form a great mass, which cannot be used. Accordingly, studies have been made intensiely about the technique for dispersing or dissolving as colloid the conjugates (M-E) of magnetic materials and physiologically by active substances such as proteins in aqueous solutions and organic solvents and consequently the present invention has been accomplished.

SUMMARY OF THE INVENTION

The present invention provides a magnetic material-physiologically active substance conjugate (M-P-E) having a magnetic material (M) and a physiologically active substance (E) bound to each other through a polyethylene glycol derivative (P) which is amphiphatic for water and an organic solvent, and also a conjugate (M-P) having M and P bound to each other to be used as the chemical modifier therefor.

DETAILED DESCRIPTION OF THE INVENTION

By selecting the molecular weight of the polyethylene glycol derivative according to the molecular weight of the physiologically active substance and the particle size of the magnetic material, dispersion stability in an organic solvent can be obtained. Generally speaking, the molecular weight should be desirably greater in order that the magnetic material-physiologically active substance conjugate (M-P-E) can be stably dissolved or dispersed in an organic solvent such as benzene. A polyethylene glycol derivative should preferably have a molecular weight of 500 to 200,000. Concerning protein which is one of physiologically active substances, for example, a polymer with a molecular weight of 1,000 or more is preferable for lysozyme with molecular weight of about 14,000; a polymer with a molecular weight of 2,000 or more for lipase with molecular weight of about 33,000; a polymer with a molecular weight of 10,000 or more for catalase with molecular weight of about 240,000. On the other hand, when a ferrite with particle size of 30 nm or larger is used as the magnetic material, a polymer with a molecular weight of 2,000 or more can be used, while a polymer with a molecular weight of 500 or more can be used for a magnetic material with a particle size smaller than 30 nm. Also, for D-asparagine with molecular weight of 132 which is one of physiologically active substances, a polymer with a molecular weight of 500 or more can be used.

As the magnetic material, there can be used transition metals or ions thereof, oxides thereof or compounds of these with other elements, for example, metals such as iron, cobalt, nickel, erbium, lutetium, dysprosium, terbium, thrium, gadlinium, or the like and oxides thereof, magnetite, ferrite, garnets, oxides with corrundum structure, oxides with perovskite structure, magnetoplumbites, oxides with rutile structure, further ferritin or highspin type deoxyhemoglobin and heme or derivatives thereof.

The reaction for preparing the magnetic material-physiologically active substance conjugate (M-P-E) of the present invention can be performed according to the two reaction schemes as shown below.

Reaction scheme (1): first, a polyethylene glycol derivative and a physiologically active substance are chemically bound together to synthesize a conjugate (P-E), and this P-E is conjugated to M synthesize M-P-E.

(i) P+E→P-E ... * 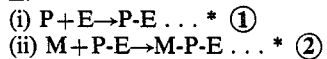
(ii) M+P-E→M-P-E ... * ②

Reaction scheme (2): first, a polyethylene glycol derivative is conjugated to M as described below to synthesize a conjugate (M-P), and this M-P is chemically bound with a physiologically active substance E to synthesize M-P-E.

(i) M+P→M-P ... * ③
(ii) M-P+E→M-P-E ... * 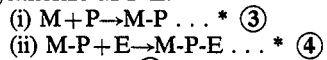

The bond * ① between P and E and the bond * ④ between M-P and E may be preferably covalent bonds, with hydroxyl group, carboxyl group, methoxycarbonyl group, amide group, amino group, methoxy group, etc. of the polyethylene glycol derivatives being covalently bonded to hydroxyl group, amino group, carboxyl group, etc. of the physiologically active substance to form, for example, acid-amide bond, ester bond, etc. In the following, their examples are shown. Here, P-0H represents a polyethylene glycol derivative having hydroxyl group and E represents a physiologically active substance and E-OH, E-NH2, E-COOH, E-SH represent physiologically active substances having hydroxyl group, amino group, carboxyl group, sulfhydryl group. (1) P-OH is allowed to react with cyanuric chloride in an inert solvent in the presence of a base to obtain an activated derivative having 1 or 2 P-OH chains bonded thereto. The activated derivative is allowed to react with a physiologically active substance in a buffered solution bound to amino oroup or hydroxyl group in the physiologically active substance molecule.

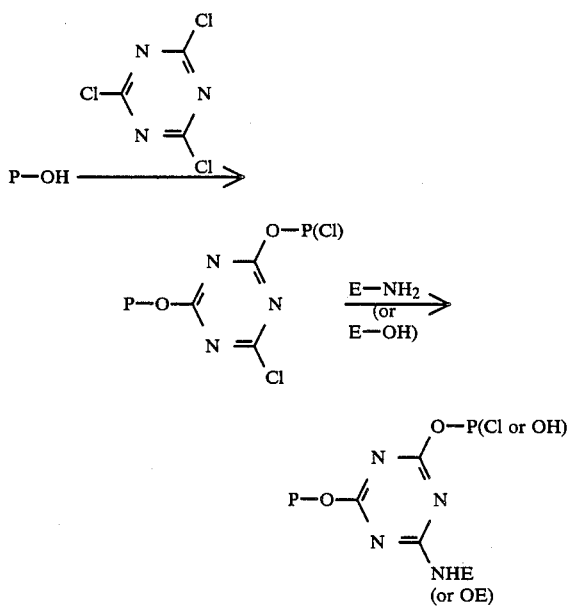

(2) Through the reaction between P-OH and bromoacetyl bromide in dibromoacetic acid and dioxane, P-bromoacetate is obtained. The acetyl derivative is allowed to react with a physiologically active substance. P-dibromosuccinate prepared by use of dibromosuccinic anhydride can be also allowed to react with a physiologically active substance.

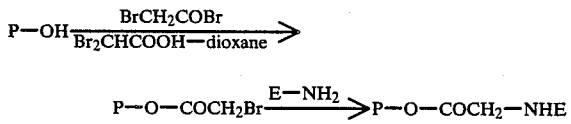

(3) As the acid azide method, P-OH is allowed to react with chloroacetic anhydride, then with diazomethane to obtain P-acetic methyl ether, which is treated with hydrazide to obtain a corresponding hydrazide, followed by treatment with sodium nitrite to obtain an acid azide derivative. This active derivative is allowed to react with a physiologically active substance to effect amide bonding with the free amino group in the physiologically active substance.

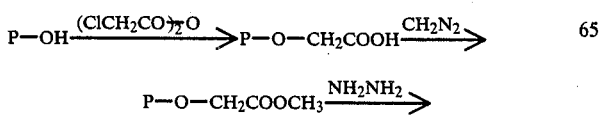

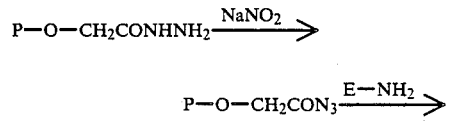

(4) As the diazo method, for example, P-OH is allowed to react with isatoic anhydride to obtain an anthranylic acid ester, then treated with sodium nitrite under acidic condition to convert it to a diazonium derivative, which is subjected to diazo coupling with a physiologically active substance.

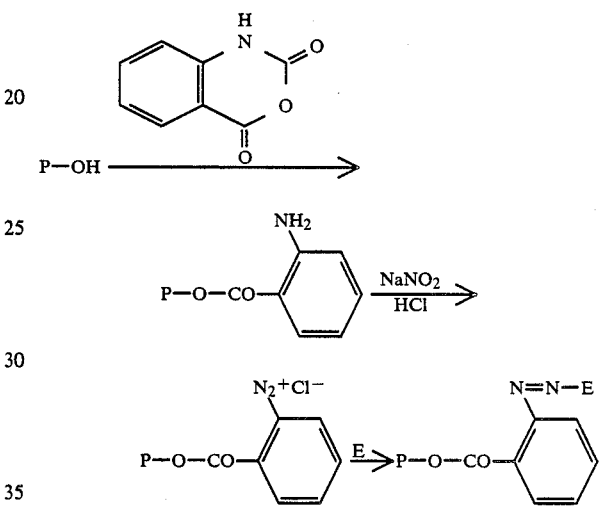

(5) The hydroxyl group of P-OH is convertible to amino group. This method comprises, for example, allowing tosyl chloride with P-OH to form P-OH-tosylate, then allowing this to react with a phthalimide salt to obtain a N-P-substituted phthalimide, which is treated with hydrazine to obtain an amphiphatic polymer, P-NH2, having amino group. This P-NH2 is allowed to react with the carboxyl group in a physiologically active substance with a carbodiimide reagent or Woodward reagent K. Alternatively, P-OH-tosylate or P-OH-bromide obtained by the reaction with a halogenating agent can be converted with sodium azide into P-OH-azide, followed by hydrogen reduction to form P-NH2.

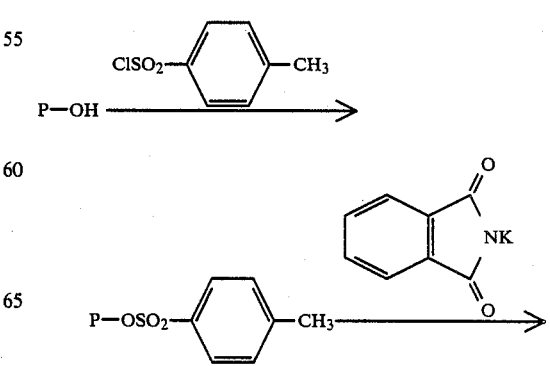

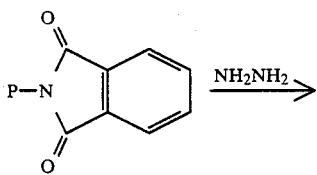

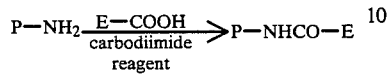

(6) The carboxylic acid derivative of P-OH, otherwise as described above, can be also allowed to react with a bromoacetic acid ester in the presence of potassium t-butoxide, followed by hydrolysis to obtain P-carboxymethyl ether. The amphiphatic polymer, P-O-CH$_2$COOH, having carboxylic acid is allowed to react wtth N-hydroxysuccinimide by utilizing a carbodiimide reagent to obtain a corresponding succinimide ester, which is allowed to react with amino group or hydroxyl group in a physiologically active substance.

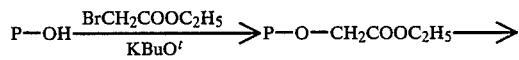

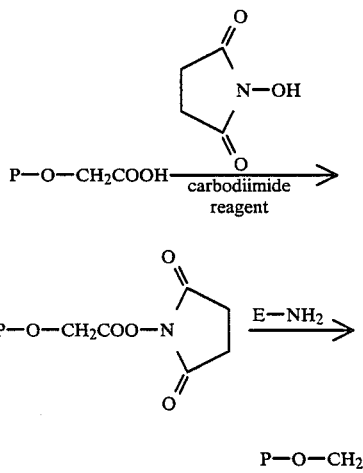

(7) Bonding of P onto the sulfhydryl group of E can be done by the above bonding method to amino group, but in order to be specifically bound to the sulfhydryl group, for example, pH is lowered to near neutral during the binding reaction by use of cyanuric chloride, or the reagent shown below exhibiting specific reactivity for the sulfhydryl group may be introduced into P.

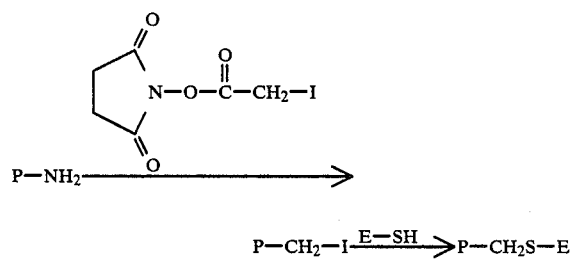

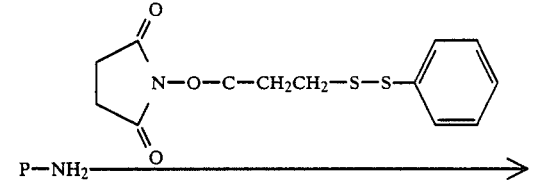

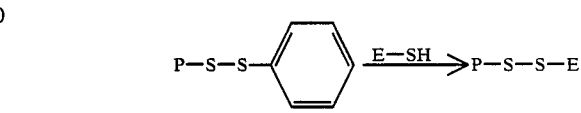

The reaction * ② in which M is bound to P-E and the reaction * ③ in which M is bound to P are magnetization reactions, and in magnetization reaction, either previously prepared magnetic material particles may be used or the formation reaction of magnetic material may be effected at the same time.

Bonding between the magnetic material and the polyethylene glycol derivative may be effected through coordination bonding or hydrogen bonding between the oxygen atom of ether bond of the polyethylene glycol skelaton or the hydrogen atom of ethylene group and hydroxyl group or metal ion on the surface of the magnetic material,.or in the case of derivatives when the polyethylene glycol has carboxyl group, hydroxyl group, methoxycarbonyl group, amide group, amino group, methoxy group, etc., through covalent bonding or coordination bonding of these groups with the hydroxyl group of the magnetic material, or coordination bonding with metal ions of the magnetic material, or through Van der Waals force between these.

Practically, the reaction for forming such bonding can be performed according to the two methods. Reaction 1: the method in which magnetic material particles are allowed to react with polyethylene glycol derivative in water or an organic solvent by means of a dispersing machine. Reaction 2: the method in which the formation reaction of a magnetic material is performed simultaneously in the presence of polyethylene glycol derivative. As the dispersing machine in Reaction 1, a ball mill, a vibrating mill, etc. can be used. By elongating the reaction time in the dispersing machine, the amount of plyethylene glycol derivative bound to magnetic material can be increased. Also, by increasing the amount of polyethylene glycol derivatie, the amount of polyethylene glycol derivative bound to magnetic material can be increased. For the formation reaction of magnetic material in Reaction 2, the reaction between ferrous ions and ferric ions under neutral-alkali condition, the reaction by oxidation of ferrous ions, the reaction between lipidocrocite or akaganecite and ferrous ions, oxidation or spontaneous transformation reaction of gneen rusts, the reaction between amorphous ferric oxide and ferrous ions, etc. can be used.

For example, 3 g of magnetite and 10 g of polyethylene glycol may be dispersed in water and, after the reaction in a ball mill for 2 days, the product is dialyzed against water to remove unreaced polyethylene glycol and obtain a magnetite-polyethylene glycol conjugate (M-P). The particle size of the magnetite-polyethylene glycol conjugate (M-P) is 30 nm, and the conjugate has 29% (weight ratio) of polyethylene glycol bound thereto. Also, the conjugate (M-P) obtained by performing the recovery operation in-a magnetic field of 6000 (Oersted) Oe in place of dialysis against water exhibits the same composition (29%). The above binding of the magnetic material with polyethylene glycol is irreversible and, as shown in Table 1, the composition (29%) will-not be changed b.y repeating dialysis in a large amount of water for any number of times or repeating magnetic separation operation, thus indicating that polyethylene glycol is bound to the magnetic material in the conjugate.

TABLE 1

| | Weight ratio of polyethylene glycol | |
|---|---|---|
| Operation times | Dialysis | Magnetic separation |
| 5 | 29% | 30% |
| 10 | 30% | 30% |
| 20 | 28% | 26% |
| 40 | 31% | 29% |

This bonding is destroyed under the condition where the magnetic material in the conjugate (M-P) is decomposed (6N HCl acidity), and this was confirmed by measurement of the IR absorption spectrum of the polyethylene glycol recovered by separation by thin layer chromatography after decomposition. This bonding is coordination bonding or hydrogen bonding between oxygen atom in the ether bond or hydrogen atom in ethylene group of polyethylene glycol and iron atom or hydroxyl group on the magnetite surface. This bonding is very stable, and the conjugate (M-P) will not be decomposed in organic solvents such as benzene, toluene, chlorofom, trichloroethylene, carbon tetrachloride, pyridine, acetone, dioxane, methanol, ethanol, dimethylformamide, dimethyl sulfoxide, etc., or in aqueous solutions of pH 4 or higher. At a pH of 3 or lower, the crystals of magnetite become unstable, whereby the conjugate (M-P) is decomposed. The ferritepolyethylene glycol conjugate (M-P) is stable even at pH 2. Even if pH may be essentially low, provided that the magnetic material itself is not decomposed, bonding between polyethylene glycol and the magnetic material is stable. If the amount of polyethylene glycol in the reaction using a ball mill is increased to 30 g, the composition of polyethylene glycol in the magnetic material-polyethylene glycol conjugate (M-P) becomes 43% (weight). Thus, the bound amount can be increased. If the reaction time in the ball mill is made 10 days, the particle size of the conjugate becomes 15 nm.

All of the above magnetite-polyethylene glycol conjugates (M-P) can be dissolved and dispersed stably in water and organic solvents, and no agglomerated particle is formed even after standing for 5 days as shown in Table 2.

TABLE 2

| Standing time (hrs.) | Formation of agglomerated particles |
|---|---|
| 0 | — |
| 0.5 | — |
| 1 | — |
| 10 | — |
| 24 | — |
| 48 | — |
| 120 | — |

It can be understood that dispersion-stability of the conjugate (M-P) according to the present invention is remarkably high, as compared with the magnetite particles having no polyethylene glycol bound thereto which is not substantially dispersed.

By use of a polyethylene glycol derivative having functional groups such as amino group, carboxyl group, etc., other than the oxygen bond in the ether bond of the polyethylene glycol skelton mentioned above, bonding also occurs between these functional groups and iron atoms and hydroxyl groups on the magnetic material surface. However, these bondings do not occur in all functional group of the polyethylene glycol derivative molecules.

For example, in the conjugate of α-methoxycarbonyl-ωmethoxy polyethylene glycol and magnetite (M-P), carboxyl groups not participating in bonding with the magnetic material remain at 10 to 30%, and also in the conjugate of α-aminopropyl-ω-methoxy polyethylene glycol and magnetite (M-P), amino groups not participating similarly in bonding remain at 25 to 50%.

The size of the magnetic material-polyethylene glycol conjugate (M-P) can be controlled by controlling the reaction time as described above in the case of carrying out the reaction by means of a dispersing machine (Reaction 1), and by changing the amount of the reagent used for formation of the magnetic material and pH during the reaction in the case of effecting simultaneously the formation reaction of the magnetic material (Reaction 2). In the method of Reaction 2, for example, when 1 g of a polyethylene glycol (average molecular weight 5,000) is allowed to react with 120 mg of ferrous chloride and 300 mo of ferric chloride at pH 8.5, a conjugate (M-P) with a partile size of 45 nm is obtained, while when reacted with decreased amounts of these iron ions, namely 64 mg of ferrous chloride and 151 mg of ferric chloride, a conjugate (M-P) with a particle size of 30 nm is obtained. On the other hand, at pH 11.0, a conjugate (M-P) of 20 nm is obtained in both cases. Dispersion stability of these conjugates in water and organic solvents is similarly high as those obtained by the reaction by means of a dispersing machine. Further, a conjugate (M-P) reacted with a polyethylene glycol having a molecular weight of 500 to 200,000 exhibits similar dispersion stability.

By use of any of the synthetic methods of the magnetic material-physiologically active substance conjugate (M-P-E) of the above two reaction schemes, by varying the molecular weight of the polyethylene glycol derivative, magnetic material-physiologically active substance conjugate (M-P-E) with the same solubility and dispersibility in organic solvents, and futher the same stability and activity can be obtained. For example, when the physiologically active substance is lipase, the magnetic material-lipase conjugate (M-P-E) obtained by use of a polyethylene glycol derivative with a molecular weight of 2,000 in the reaction scheme (1) and the magnetic material-lipase conjugate (M-P-E) obtained by use of a polyethylene glycol derivative with a molecular weight of 10,000 in the reaction scheme (2) have the same properties.

The size of the magnetic material-physiologically active substance conjugate (M-P-E) particles, when employing previously prepared magnetic material, becomes the size of the magnetic material particles, while it is determined depending on the P-E (the reaction scheme (1)) or P (the reaction scheme (2)) and the amounts of the reagents for formation of the magnetic material when the formation reaction of the magnetic material is performed. For example, in the case of using a ferrite with a particle size of 50 nm, it becomes a magnetic material-physiologically active substance conjugate (M-P-E) with a particle size of 50 nm. On the other hand, when 1 g of a polyethylene glycol-lipase conjugate (P-E) is allowed to react with 64 mg of ferrous chloride and 151 mg of ferric chloride, a conjugate (M-P-E) with a particle size of 30 nm is obtained, and when the amounts of these iron ions are decreased, for example, to 6.4 mg of ferrous chloride and 15 mg of ferric chloride, a conjugate (M-P-E) with a particle size of 10 nm is obtained.

Physiological activity of the magnetic material- physiologically active substance conjugate (M-P-E), for example, enzyme activity depends on its particle size, and the activity is greater as the particle size is smaller. This is because the surface area of the particles is increased as the particle size is smaller. For example, when the ester synthetic activity in benzene of the magnetic material-lipase conjugate (M-P-E) synthesized by use of a polyethylene glycol derivative is compared with a polyethylene glycol-lipase conjugate (P-E in the above reaction scheme (1)), the activities of the magnetic material-lipase conjugates (M-P-E) with particle sizes of 70 nm and 10 nm are respectively 10% and 95% of that of the polyethylene glycol-lipase conjugate (P-E).

The magnetic material-physiologically active conjugate (M-P-E) is stably dispersed in an aqueous solution and an organic solvent. For example, the magnetic material-lipase conjugate (M-P-E) will not be sedimented by centrifugation in benzene at 2,000×g for 5 minutes, but can be dispersed and dissolved in aqueous solutions and organic solvents such as benzene for about 2 days to 7 days.

The magnetic material-physiologically active substance conjugate (M-P-E) in which the constituting magnetic material is a ferromagnetic material with a particle size of about 30 nm can be separated by a permanent magnet and an electromagnet, and while the other magnetic materials, by superconductive electromagnets irrespectively of their particle sizes. For example, a ferromagnetic material (ferrite)-lipase conjugate (M-P-E) with a particle size of about 70 nm can be recovered in a magnetic field of 300 Oersted (Oe) by use of permanent magnets at a distance of 1.7 cm in 5 minutes at 100% recovery. On the other hand, with particle size of 30 nm, 100% recovery is possible in 7 minutes in a magnetic field of 5,000 Oe by use of electromagnets at a distance of 1.7 cm. The paramagnetic material (erbium)-physiologically active conjugate (M-P-E) can be recovered at 100% in 5 minutes in a magnetic field of 2 Tesla (T)=20,000 Oe by use of a superconductive electromagnet.

The present invention is applicable for enzyme, protein, antibody, antigen, polysaccharide, nucleic acid, lipid, amino acid, co-enzyme (NAD+, NADP+, etc.), high energy phosphoric acid compound (ATP, ADP, etc.), prosthetic group (heme, riboflavin, etc.), hormone, vitamin, receptor, ligand, antibiotic, antitumor substance, pharmaceutical, or chloroplast, mitochondrion, virus, cell and constituents thereof, which are physiologically active substances. For example, as the enzyme, hydroxylases such as lipase, esterase, chymotrypsin, trypsin, subtilicin, redoxidases such as peroxidase, catalase, may be preferably used when the substrate or the product is water-insoluble, including the case when the reaction can be proceeded reversibly by carrying out the reaction in an organic solvent. In the case of using a co-enzyme, the enzymatic reaction requiring a co-enzyme such as alcohol dehydrogenation reaction can be carried out. When using ATP, ADP, etc., the present invention can be utilized for the enzymatic reaction in which these are used as the substrate. Also, by use of such substances as specific antibodies, concanavalin A, polysaccharides, amino acids, vitamins, lipids, hormones, viruses, substances having affinity for these substances can be separated, purified and recovered. Further, when antibiotics, antitumor substances, pharmaceuticals are used, since magnetic properties can be imparted to these substances, they can be made amphiphatic pharmaceuticals having magnetic properties.

The specific feature of the present invention resides in that the magnetic material and the physiologically active substance are bound to each other through a polyethylene glycol derivative. Consequently, the following effects may be contemplated. (1) The magnetic material-physiologically active substance conjugate (M-P-E) can be recovered rapidly and simply by magnetic separation through its magnetic properties from in aqueous solutions and in organic solvents. (2) Due to amphiphatic property possessed by the polymer, the magnetic material-physiologically active substance conjugate (M-P-E) can be dissolved or dispersed as colloid in aqueous solutions and organic solvent. (3) Organic synthetic reaction or exhibition of biological activity which have been impossible in bio-reactors using aqueous solutions of the prior art are rendered possible. (4) The magnetic material-physiologically active substance conjugate (M-P-E) can be dissolved or dispersed again in the solvent employed for reuse. (5) When used as a pharmaceutical, irrespectively of whether the afflicted site is under hydrophobic or hydrophilic environment, the pharmaceutical can be magnetically led to the afflicted site.

The present invention is described below by referring to Examples.

EXAMPLE 1

(a) To a solution of 5 g (2.5 mmol) of $\alpha,\omega$-dicarboxy polyethylene glycol (average molecular weight 2,000) and 288 mg (2.5 mmol) of N-hydroxysuccinic imide dissolved in 15 ml of dimethylformamide was added 1 ml of dimethylformamide containing 618 mg of dicyclohexylcarbodiimide to activate the carboxyl groups of the polyethylene glycol derivative. Into 20 ml of an aqueous phosphate buffered solution (pH 7.0) containing 200 mg of lipase obtained from *Pseudomonas fluorescens* cells was added 2 g of the above activated polyethylene glycol derivative, followed by the reaction at 25° C. for 1 hour to obtain a polyethylene glycol-lipase conjugate (P-E).

A solution of 1 g of the polyethylene glycol-lipase conjugate (P-E) dissolved in 1.3 ml of water was adjusted to pH 8.0 with ammonia water, and 0.6 ml of an aqueous solution containing 64 mg of ferrous chloride and 151 mg of ferric chloride was added dropwise to this solution. During the dropwise addition, pH was maintained at 8.0 to 8.5 with ammonia water, and the mixture was well stirred at room temperature. After sufficiently dialyzed against water, a magnetic material-lipase conjugate (M-P-E) was obtained by lyophilization.

The magnetic material-lipase conjugate (M-P-E) was found to contain 34% of the magnetic material and 30% of the protein. Also, it had a hydrolysis activity of olive oil in water of 1500 units/mg protein, and a synthetic activity of lauryl laurate of 10 $\mu$mol/min./mg protein in benzene which is a representative hydrophobic organic solvent. The magnetic-lipase conjugate (M-P-E) was completely recovered from the reaction solution in 5 minutes in a magnetic field of 6,000 Oersted (Oe). This was again dissolved as colloid in the reaction solution to exhibit similar activities.

It was found that the magnetic material-lipase conjugate (M-P-E) dissolved as colloid in the aqueous solution and benzene was not sedimented by centrifugation at 2,000×g, and its turbidity did not change for 24 to 60 hours in turbidity measurement at 600 nm. Thus the conjugate stably dispersed in an organic solvent. Also, in the aqueous solution, similar dispersion stability was observed. By observation with an electron microscope, the conjugate was found to consist of ultra-fine particles with particle sizes of 10 to 40 nm.

As to organic solvents other than benzene, in solvents in which the amphiphatic polymer used here is soluble such as toluene, chloroform, chlorinated hydrocarbons, etc., the magnetic material-lipase conjugate (M-P-E) exhibited similar properties.

(b) Also by use of $\alpha,\omega$-dicarboxy polyethylene glycols with molecular weights of 5,000 and 20,000 in place of the $\alpha,\omega$-dicarboxy polyethylene glycol with molecular weight of 2,000, magnetic material-lipase conjugates (M-P-E) having similar properties were obtained.

(c) Also by use of $\alpha$-amino-$\omega$-carboxy polyethylene glycol (molecular weight 2,000), $\alpha$-carboxy-$\omega$-methoxy polyethylene glycol (molecular weight 2,000) or 2,4-bis(methoxypolyoxyethylene)-6-chloro-S-triazine (molecular weight 10,000) in place of $\alpha,\omega$-dicarboxy polyethylene glycol, a magnetic material-lipase conjugate having similar properties was obtained.

(d) Also from the polyethylene glycol-lipase conjugate (P-E) obtained by use of $\alpha,\omega$-diamino polyethylene glycol in place of $\alpha,\omega$-dicarboxy polyethylene glycol, a similar magnetic material-lipase conjugate (M-P-E) was obtained. The polyethylene glycol-lipase conjugate (P-E) was obtained by adding 200 mg of a water-soluble carbodiimide into 20 ml of an aqueous phosphate buffered solution (pH 7.0) containing 2 g of $\alpha,\omega$-diamino polyethylene glycol and 200 mg of lipase and carrying out the reaction at 37° C. for 30 minutes, followed by dialysis against water.

EXAMPLE 2

According to the method of Example 1a) by use of 150 mg of subtilicin derived from *Bacillus subtilis* in place of lipase, a magnetic material-subtilicin conjugate (M-P-E) was obtained. The magnetic material-subtilicin conjugate (M-P-E) contained 36% of the magnetic material and 25% of the protein. Also, it had a hydrolysis activity of ethyl acetyltyrosinate in aqueous solution of 600 units/mg protein, and a synthetic activity of N-benzoyltyrosine butylamide of 4.0 $\mu$mol/min./mg protein in benzene which is a representative hydrophobic organic solvent. The magnetic material-subtilicin conjugate (M-P-E) was completely recovered from the reaction solution in 5 minutes in a magnetic field of 5,500 Oersted (Oe). This was dissolved again as colloid in the reaction solution to exhibit similar activities. Dispersion stability, the particle size and other properties of the magnetic material-subtilicin conjugate (M-P-E) dissolved as colloid in the aqueous solution and the organic solvent were found to be the same as the above magnetic material-lipase conjugate (M-P-E).

EXAMPLE 3

According to the method of Example 1a) by use of 70 mg of catalase derived from bovine liver in place of lipase, a magnetic material-catalase conjugate (M-P-E) was obtained. The magnetic material-catalase conjugate (M-P-E) contained 25% of the magnetic material and 45% of the protein. Also, it had a decomposition activity of hydrogen peroxide in aqueous solution of 60,000 units/mg protein, and a decomposition activity of hydrogen peroxide of 70,000 units/mg protein in benzene which is a representative hydrophobic organic solvent. The magnetic material-catalase conjugate (M-P-E) was recovered completely from the reaction solution in 7 minutes in a magnetic field of 6,000 Oersted (Oe). This was again dissolved as colloid in the reaction solution to exhibit similar activities. Dispersion stability and the particle size of the magnetic material-catalase conjugate (M-P-E) dissolved as colloid in the aqueous solution and the organic solvent were found to be the same as the above magnetic material-lipase conjugate (M-P-E).

Also, similar results were obtained by use of esterase in place of lipase.

EXAMPLE 4

A solution of 5 g of $\alpha,\omega$-dicarboxy polyethylene glycol (molecular weight 2,000) dissolved in 5 ml of water was adjusted to pH 8.0 with an aqueous ammonia, and to this solution was added dropwise 2.4 ml of distilled water containing 250 mg of ferrous chloride, 50 mg of cobalt chloride and 750 mg of ferric chloride. During the dropwise addition, pH was maintained at 8.0 to 8.5 with an aqueous ammonia, and the mixture was stirred sufficiently at 60° C. The reaction mixture was sufficiently dialyzed against water to obtain a magnetic material-polyethylene glycol conjugate (M-P).

Into 4 ml of a phosphate buffered solution (pH 7.0) containing 5 mg of lipase obtained from *Pseudomonas fluorescens* cells and 75 mg of the magnetic material-polyethylene glycol conjugate (M-P) was added 500 mg of a water-soluble carbodiimide and, after the reaction at 37° C. for 90 minutes, 5 ml of water was added to the reaction mixture. The magnetic material-lipase conjugate (M-P-E) formed by magnetic separation was thoroughly washed with water and then lyophilized to obtain a magnetic-lipase conjugate (M-P-E).

The magnetic material-lipase conjugate (M-P-E) was found to contain 50% of the magnetic material and 20% of the protein. Also, it had a hydrolysis activity of olive oil in water of 500 units/mg protein, and a synthetic activity of lauryl laurate of 1.5 $\mu$mol/min./mg protein in benzene which is a representative hydrophobic organic solvent. The magnetic-lipase conjugate (M-P-E) was completely recovered from the reaction solution in 5 minutes in a magnetic field of 300 Oersted (Oe). This was again dissolved as colloid in the reaction solution to exhibit similar activities.

It was found that the magnetic material-lipase conjugate (M-P-E) dissolved as colloid in the aqueous solution and benzene was not sedimented by centrifugation at 2,000×g, and its turbidity did not change for 24 to 60 hours in measurement at 600 nm. Thus the conjugate stably dispersed in an organic solvent. Also, in the aqueous solution, similar dispersion stability was observed. By observation with an electron microscope, the conjugate was found to consist of ultra-fine particles with particle sizes of 60 to 100 nm.

As to organic solvents other than benzene, in solvents in which the amphiphatic polymer used here is soluble such as toluene, chloroform, chlorinated hydrocarbons, etc., the magnetic material-lipase conjugate (M-P-E) exhibited similar properties. Also, to the carboxyl groups of the magneic materialpolyethylene glycol conjugate (M-P) was bound N-hydroxysuccinimide according to a conventional method in dioxane to synthesize an activated matnetic material-polyethylene glycol conjugate (M-P). And, 75 mg of the activated magnetic material-polyethylene glycol conjugate (M-P) was added to 4 ml of a phosphate bufferd solution (pH 7.0) containing 5 mg of lipase obtained from *Pseudomonas fragi* 22-39B cells and, after the reaction at 37° C. for 90 minutes, the reaction product was purified to obtain a magnetic material-lipase conjugate having similar properties.

EXAMPLE 5

A solution of 5 g of α,ω-dicarboxy polyethylene glycol (average molecular weight 2,000) and 150 mg of ferrous chloride dissolved in 4 ml of water was adjusted to pH 8.0 with an aqueous ammonia, and oxidized by passing oxygen at 65° C. for 1 hour. The reaction mixture was thoroughly dialyzed against water to obtain a magnetic material-polyethylene glycol conjuqate (M-P). To the carboxyl groups of the magnetic material-polyethylene glycol (M-P) was bound N-hydroxysuucinimide according to a conventional method to synthesize an activated magnetic materil-polyethylene glycol conjugate (M-P). And, 75 mg of the activated magnetic material-polyethylene glycol conjugate (M-P) was added to 4 ml of a phosphate buffered solution (pH 7.0) containing 5 mg of lipase obtained from *Pseudomonas fluorescens* cells and, after the reaction at 37° C. for 90 minutes, the magnetic material-lipase conjugate (M-P-E) formed by magnetic separation was thoroughly washed with water, followed by lyophilization, to give a magnetic material-lipase conjugate (M-P-E). Dispersibility or magnetic separation characteristics, etc. of this conjugate were found to be the same as the magnetic material-lipase conjugate (M-P-E) in Example 1.

EXAMPLE 6

In a suspension of 5 g of α,ω-dicarboxy polyethylene glycol (average molecular weight 2,000) and Y-FeOOH (100 mg in amount of iron) in 5 ml of water, ferrous chloride (50 mg in amount of iron) was dissolved. The solution was adjusted to pH 8.0 and left to stand in a nitrogen gas stream at 60° C. for 1 hour. The reaction mixture was sufficiently dialyzed against water to obtain a magnetic material-polyethylene glycol conjugate (M-P). To the carboxyl groups of the magnetic material-polyethylene glycol (M-P) was bound N-hydroxysuccinimide according to a conventional method to synthesize an activated magnetic material-polyethylene glycol conjugate (M-P). And, 75 mg of the activated magnetic material-polyethylene glycol conjugate (M-P) was added to 4 ml of a phosphate buffered solution (pH 7.0) containing 5 mg of lipase obtained from *Pseudomonas fluorescens* cells and, after the reaction at 37° C. for 90 minutes, the magnetic material-lipase conjugate (M-P-E) formed by magnetic separation was thoroughly washed with water, followed by lyophilization, to give a magnetic material-lipase conjugate (M-P-E). Dispersibility or magnetic separation characteristics, etc. of this conjugate were found to be the same as the magnetic material-lipase conjugate (M-P-E) obtained in Example 1.

EXAMPLE 7

To 5 ml of chloroform containing 5 g of α,ω-dicarboxy polyethylene glycol (average molecular weight 4,000) was added 500 mg of erbium oxide (particle size 200 nm), and the mixture was pulverized in a ball mill for 7 days, followed by complete removal of chloroform, to obtain a magnetic material-polyethylene glycol conjugate (M-P). To the carboxyl groups of the magnetic materialpolyethylene glycol conjugate (M-P) was bound N-hydroxysuccinimide according to a conventional method to synthesize an activated magnetic material-polyethylene glycol conjugate (M-P).

And, 75 mg of the activated magnetic material-polyethylene glycol conjugate (M-P) was added to 4 ml of a phosphate buffered solution (pH 7.0) containing 5 mg of lipase obtained from *Pseudomonas fluorescens* cells and, after the reaction at 37° C. for 90 minutes, the product was purified to obtain a magnetic material-lipase conjugate (M-P-E) having similar properties.

The magnetic material-lipase conjugate (M-P-E) was found to contain 45% of the magnetic material and 20% of the protein. Also, it had a hydrolysis activity of olive oil in water of 650 units/mg protein, and a synthetic activity of lauryl laurate of 2.5 μmol/min./mg protein in benzene which is a representative hydrophobic organic solvent. The magnetic material-lipase conjugate (M-P-E) was completely recovered from the reaction solution (5 mg/ml) in 5 minutes in a magnetic field of 20,000 Oersted (Oe)=2 Tesla (T) in the presence of steel wool. This was again dissolved as colloid in the reaction solution to exhibit similar activities.

It was found that the magnetic material-lipase conjugate (M-P-E) dissolved as colloid in the aqueous solution and benzene was not sedimented by centrifugation at 2000×g, and its turbidity did not change for 24 to 60 hours in turbidity measurement at 600 nm. Thus the conjugate stably dispersed in an organic solvent. Also, in the aqueous solution, similar dispersion stability was observed. By observation with an electron microscope, the conjugate was found to consist of ultra-fine particles with particle sizes of 90 nm.

As to organic solvents other than benzene, in solvents in which the amphiphatic polymer used here is soluble such as toluene, chloroform, chlorinated hydrocarbons, etc., the magnetic material-lipase conjugate (M-P-E) exhibited similar properties.

EXAMPLE 8

(a) A 5 ml of an aqueous solution of 20 mM 1,4-piperazine7,30bis(ethanesulfonic acid) containing 5 g of α-carboxy-ω-methoxy polyethylene glycol (average molecular weight 4,000) and 200 mg of dysprosium chloride was prepared and pH is raised to 7.0 to 7.5 with addition of sodium hydroxide to the solution. After the solution was subjected to dialysis against water or gel filtration to remove salts, it was lyophilized to give a magnetic material-polyethylene glycol conjugate (M-P). To the carboxyl groups of the magnetic material-polyethylene qlycol conjugate (M-P) was bound N-hydroxysuccinimide according to a conventiona method to synthesize an activated magnetic material-polyethylene glycol conjugate (M-P).

And, 75 mg of the activated magnetic material-polyethylene glycol conjugate (M-P) was added to 4 ml of a phosphate buffered solution (pH 7.0) containing 5 mg of lipase obtained from *Pseudomonas fluorescens* cells and, after the reaction at 37° C. for 90 minutes, the product was purified to obtain a magnetic material-lipase conjugate (M-P-E) having similar properties.

The magnetic material-lipase conjugate (M-P-E) was found to contain 20% of the magnetic material and 35% of the protein. Also, it had a hydrolysis activity of olive oil in water of 750 units/mg protein, and a synthetic activity of lauryl laurate of 8.5 μmol/min./mg protein in benzene which is a representative hydrophobic organic solvent. The magnetic material-lipase conjugate (M-P-E) was completely recovered from the reaction solution (5 mg/ml) in 5 minutes in a magnetic field of 20,000 Oersted (Oe)=2 Tesla (T) in the presence of steel wool. This was again dissolved as colloid in the reaction solution to exhibit similar activities.

It was found that the magnetic material-lipase conjugate (M-P-E) dissolved as colloid in the aqueous solution and benzene was not sedimented by centrifugation at 10,000×g, and its turbidity did not change for 24 to 60 hours in turbidity measurement at 600 nm. Thus the conjugate stably dispersed in an organic solvent. Also, in the aqueous solution, similar dispersion stability was observed. As to organic solvents other than benzene, in solvents in which the amphiphatic polymer used here is solube such as toluene, chloroform, chlorinated hydrocarbons, etc., the magnetic material-lipase conjugate (M-P-E) exhibited similar properties.

(b) Similar results were obtained by use of α,ω-dicarboxy polyethylene glycol (average molecular weight 4,000) or an activated polyethylene glycol (average molecular weight 5,000) in place of the α-carboxy-ω-methoxy polyethylene glycol (average molecular weight 4000). Here, in the case of the activated polyethylene glycol or the activated polypropylene glycol, a magnetic materialpolyethylene glycol conjugate (M-P) having the hydroxyl group activated with cyanuric chloride was used, and further the reaction with lipase was carried out in a borate buffered solution of pH 9.5 at 4° C. for 5 hours to obtain a magnetic material-lipase conjugate (M-P-E).

EXAMPLE 9

To a solution of 5 g (2.5 mmol) of α,ω-dicarboxy polyethylene glycol (average molecular weight 20,000) and 288 mg (2.5 mmol) of N-hydroxysuccinimide dissolved in 15 ml of dimethylformamide, 1 ml of dimethylformamide containing 0.618 mg of dicyclohexylcarbodiimide to activate one carboxyl group of the polyethylene glycol derivative. By addition of 2 g of the above activated polyethylene glycol derivative to 20 ml of an aqueous phosphate buffered solution (pH 7.0) containing 200 mg of ferritin, the reaction was carried out at 25° C. for 1 hour and, after ultrafiltration and dialysis against water, a magnetic material-polyethylene glycol conjuqate (M-P) was obtained.

To 4 ml of a phosphate buffered solution (pH 7.0) containing 5 mg of lipase obtained from *Pseudomonas fluorescens* cells and 75 mg of the magnetic material-polyethylene glycol conjugate (M-P), 500 mg of a water-soluble carbodiimide was added and, after the reaction at 37° C. for 90 minutes, 5 ml of water was added to the reaction mixture. The magnetic material-lipase conjugate (M-P-E) formed by magnetic separation was thoroughly washed with water, and then lyophilized to obtain a magnetic material-lipase conjugate (M-P-E).

The magnetic material-lipase conjugate (M-P-E) was found to contain 60% of the magnetic material and 5% of the protein. Also, it had a hydrolysis activity of olive oil in water of 750 units/mg protein, and a synthetic activity of lauryl laurate of 9.5 umol/min./mg protein in benzene which is a representative hydrophobic organic solvent. The magnetic material-lipase conjugate (M-P-E) was completely recovered from the reaction solution (5 mg/ml) in 5 minutes in a magnetic field of 20,000 Oersted (Oe)=2 Tesla (T) in the presence of steel wool. This was again dissolved as colloid in the reaction solution to exhibit similar activities.

It was found that the magnetic material-lipase conjugate (M-P-E) dissolved as colloid in the aqueous solution and benzene was not sedimented by centrifugation at 10,000×g, and its turbidity did not change for 24 to 60 hours in turbidity measurement at 600 nm. Thus the conjugate stably dispersed in an organic solvent. Also, in the aqueous solution, similar dispersion stability was observed. By electron microscope observation, the conjugate was found to consist of ultra-fine particles with particle size of 5 nm. po As to organic solvents other than benzene, in solvents in which the amphiphatic polymer used here is soluble such as toluene, chloroform, chlorinated hydrocarbons, etc., the magnetic material-lipase conjugate (M-P-E) exhibited similar properties.

EXAMPLE 10

To a solution of 12.5 g (2.5 mmol) of α,ω-diamino polyethylene glycol (average molecular weight 5,000) and 144 mg (1.25 mmol) of hemine dissolved in 20 ml of pyridine, 1 ml of dimethylformamide containing 1.2 mg of dicyclohexylcarbodiimide was added and the reaction was carried out at 60° C. for 6 hours. After filtration of the reaction solution, pyridine was removed by evaporation. The residue was dissolved in water and insolubles were removed by centrifugation, followed by lyophilization, to obtain a magnetic material-polyethylene glycol conjugate (M-P).

To 4 ml of a phosphate buffered solution (pH 7.0) containing 5 mg of lipase obtained from *Pseudomonas fluorescens* cells and 75 mg of the magnetic material-polyethylene glycol conjugate (M-P), 500 mg of a water-soluble carbodiimide was added and, after the reaction at 37° C. for 90 minutes, 5 ml of water was added to the reaction mixture. The magnetic material-lipase conjugate (M-P-E) formed by magnetic separation was thoroughly washed with water, and then lyophilized to obtain a magnetic material-lipase conjugate (M-P-E).

The magnetic material-lipase conjugate (M-P-E) was found to contain 20% of the magnetic material and 30% of the protein. Also, it had a hydrolysis activity of olive oil in water of 750 units/mg protein, and a synthetic activity of lauryl laurate of 8.5 umol/min./mg protein in benzene which is a representative hydrophobic organic solvent. The magnetic material-lipase conjugate (M-P-E) was completely recovered from the reaction solution (5 mg/ml) in 5 minutes in a magnetic field of 20,000 Oersted (Oe)=2 Tesla (T) in the presence of steel wool. This was again dissolved as colloid in the reaction solution to exhibit similar activities.

It was found that the magnetic material-lipase conjugate (M-P-E) dissolved as colloid in the aqueous solution and benzene was not sedimented by centrifugation at 10,000×g, and its turbidity did not change for 24 to 60 hours in turbidity measurement at 600 nm. Thus the conjugate stably dispersed in an organic solvent. Also, in the aqueous solution, similar dispersion stability was observed. By electron microscope observation, the conjugate was found to consist of ultra-fine particles with particle size of 5 nm.

As to organic solvents other than benzene, in solvents in which the amphiphatic polymer used here is soluble such as toluene, chloroform, chlorinated hydrocarbons, etc., the magnetic material-lipase conjugate (M-P-E) exhibited similar properties.

EXAMPLE 11

According to a conventional method, $N^6$-(2-carboxyethyl)NAD$^+$ having carboxyl groups introduced into NAD$^+$ was synthesized. To a solution of 5 g of α-amino-ω-methoxy polyethylene glycol (average molecular weight 2,000) and 0.6 g of $N^6$-(2-carboxyethyl)-NAD$^+$ dissolved in water, 5 g of a water-soluble carbodiimide was added, and the reaction was carried out at pH maintained at 4.5 for 20 hours. After extraction with chloroform, the extract was purified by ion exchange to give a polyethylene glycol-NAD$^+$ conjugate (P-E).

A solution of 1 g of the polyethylene glycol-NAD$^+$ conjugate (P-E) dissolved in 1.3 ml of water was adjusted to pH 8.0 with ammonia water, and 0.6 ml of an aqueous solution containing 64 mg of ferrous chloride and 151 mg of ferric chloride was added dropwise. During the dropwise addition, pH was maintained at 8.0 to 8.5 with ammonia water, and the mixture was well stirred at room temperature. After sufficiently dialysed against water, the product was lyophilized to give a magnetic material-NAD$^+$ conjugate (M-P-E).

The magnetic material-NAD$^+$ conjugate (M-P-E) contained 80% of the magnetic material and 3% of the co-enzyme. The magnetic material-NAD$^+$ conjugate (M-P-E) was dispersed or dissoled as colloid in aqueous solutions and organic solvents such as benzene, toluene, chloroform, chlorinated hydrocarbons, and completely recovered from these solutions in 5 minutes in a magnetic field of 6,000 Oersted (Oe). This was again dissolved as colloid in the reaction solution.

It was found that the magnetic material-NAD$^+$ conjugate (M-P-E) dissolved as colloid in the aqueous solution and organic solvents was not sedimented by centrifugation at 2,000×g, and its turbidity did not change for 24 to 60 hours in turbidity measurement at 600 nm. Thus the conjugate stably dispersed in an organic solvent. Also, in the aqueous solution, similar dispersion stability was observed. By electron microscope observation, the conjugate was found to consist of ultra-fine particles with particle sizes of 20 to 40 nm.

The magnetic material-NAD$^+$ conjugate (M-P-E) exhibited activity as a co-enzyme and, for example, was converted to a magnetic material-NADH conjugate (M-P-E) by alcohol dehydrogenase treatment together with ethyl alcohol.

Also by use of NADP$^\oplus$ in place of NAD$^+$, a magnetic material-NADP$^+$ conjugate (M-P-E) having similar properties was obtained.

EXAMPLE 12

A solution of 1.2 g of α,ω-dicarboxy polyethylene glycol (average molecular weight 4,000) dissolved in 0.8 ml of distilled water was adjusted to pH 8.0 with an aqueous ammonia and to this solution was added 0.4 ml of water containing 120 mg of ferrous chloride and 51 mg of ferric chloride. During the dropwise addition, pH was maintained at 8.0 to 8.5 with an aqueous ammonia, and the mixture was well stirred at 60° C. After sufficient dialysis of the reaction mixture against water, a magnetic material-polyethylene glycol conjugate (M-P) was obtained.

To 2 ml of a phosphate buffered solution (pH 5.0) containing 100 mg of ADP and 500 mg of the magnetic material-polyethylene glycol conjugate (M-P), 500 mg of a water-soluble carbodiimide was added and, after the reaction at 37° C. for 12 hours, 5 ml of water was added to the reaction mixture. The magnetic material-ADP conjugate (M-P-E) formed was thoroughly washed with water by magnetic separation, and then lyophilized to obtain a magnetic material-ADP conjugate (M-P-E).

The magnetic material-ADP conjugate (M-P-E) was found to contain 85% of the magnetic material and 3% of the co-enzyme. The magnetic material-ADP conjugate (M-P-E) was dispersed or dissolved as colloid in aqueous solutions and organic solvents such as benzene, toluene, chloroform, chlorinated hydrocarbons, and completely recovered from these solutions in 5 minutes in a magnetic field of 6,000 Oersted (Oe). This was again dissolved as colloid in the reaction solution.

It was found that the magnetic material-ADP conjugate (M-P-E) dissolved as colloid in the aqueous solution and organic solvents was not sedimented by centrifugation at 2,000×g, and its turbidity did not change for 24 to 60 hours in turbidity measurement at 600 nm. Thus the conjugate stably dispersed in an organic solvent. Also, in the aqueous solution, similar dispersion stability was observed. By electron microscope observation, the conjuqate was found to consist of ultra-fine particles with particle sizes of 10 to 40 nm.

The magnetic material-ADP conjugate (M-P-E) exhibited activity and, for example, was converted to a magnetic material-ATP conjugate (M-P-E) by pyruvate kinase treatment together with phosphoenol pyruvic acid.

Also by use of ATP in place of ADP, a magnetic material-ATP conjugate (M-P-E) could be obtained.

EXAMPLE 13

The carboxyl groups of α,ω-dicarboxy polyethylene glycol (average molecular weight 4,000) are activated according to the method of Example 1a). By addition of the prepared activated polyethylene glycol derivative (600 mg) to 10 ml of an aqueous phosphate buffered solution (pH 7.0) containing anti-asparaginase antibody (100 mg) obtained from a rabbit imminized with asparaginase, the reaction was carried out at 25° C. for 90 minutes to obtain a polyethylene glycol-antibody conjugate (P-E).

A solution of 1 g of the polyethylene glycol-antibody (P-E) dissolved in 1.3 ml of water was adjusted to pH 8.0 with an aqueous ammonia and to this solution was added 0.6 ml of aqueous solution containing 64 mg of ferrous chloride and 151 mg of ferric chloride. During the dropwise addition, pH was maintained at 8.0 to 8.5 with an aqueous ammonia, and the mixture was well stirred at room temperature. After sufficient dialysis of the reaction mixture against water, a magnetic material-antibody conjugate (M-P-E) was obtained by lyophilization.

The magnetic material-antibody conjugate (M-P-E) was found to contain 34% of the magnetic material and 25% of the protein. The magnetic material-antibody conjugate (M-P-E) was dispersed or dissolved as colloid in aqueous solutions and organic solvents such as benzene, toluene, chloroform, chlorinated hydrocarbons, and completely recovered from these solutions in 5 minutes in a magnetic field of 6,000 Oersted (Oe). This was again dissolved as colloid in the reaction solution.

It was found that the magnetic material-antibody conjugate (M-P-E) dissolved as colloid in the aqueous solution and organic solvents was not sedimented by centrifugation at 2,000×g, and its turbidity did not change for 24 to 60 hours in turbidity measurement at 600 nm. Thus the conjugate stably dispersed in an organic solvent. Also, in the aqueous solution, similar dispersion stability was observed. By electron microscope observation, the conjugate was found to consist of ultra-fine particles with particle sizes of 10 to 40 nm.

The magnetic material-antibody conjugate had high affinity for asparaginase, and had an activity of 70% per antibody as compared with the anti-asparaginase antibody forming no conjugate with the magnetic material.

EXAMPLE 14

The carboxyl groups of α,ω-dicarboxy polyethylene glycol (average molecular weight 4,000) are activated according to the method of Example 1a). By addition of the prepared activated polyethylene glycol derivative (600 mg) to 10 ml of an aqueous phosphate buffered solution (pH 7.0) containing concanavalin A (100 mg), the reaction was carried out at 25° C. for 90 minutes to obtain a polyethylene glycol-concanavalin A conjugate (P-E).

A solution of 1 g of the polyethylene glycol-concanavalin A (P-E) dissolved in 1.3 ml of water was adjusted to pH 8.0 with an aqueous ammonia and to this solution was added 0.6 ml of aqueous solution containing 64 mg of ferrous chloride and 151 mg of ferric chloride. During the dropwise addition, pH was maintained at 8.0 to 8.5 with an aqueous ammonia, and the mixture was well stirred at room temperature. After sufficient dialysis of the reaction mixture against water, a magnetic materialconcanavalin A conjugate (M-P-E) was obtained by lyophilization.

The magnetic material-concanavalin A conjugate (M-P-E) was found to contain 56% of the magnetic material and 25% of concanavalin A. The magnetic material-concanavalin A conjugate (M-P-E) was dispersed or dissolved as colloid in aqueous solutions and organic solvents such as benzene, toluene, chloroform, chlorinated hydrocarbons, and completely recovered from these solutions in 5 minutes in a magnetic field of 6,000 Oersted (Oe). This was again dissolved as colloid in the reaction solution.

It was found that the magnetic material-concanavalin A conjugate (M-P-E) dissolved as colloid in the aqueous solution and organic solvents was not sedimented by centrifugation at 2,000×g, and its turbidity did not change for 24 to 60 hours in turbidity measurement at 600 nm. Thus the conjugate stably dispersed in an organic solvent. Also, in the aqueous solution, similar dispersion stability was observed. By electron microscope observation, the conjugate was found to consist of ultra-fine particles with particle sizes of 10 to 40 nm.

When the magnetic material-concanavalin A conjugate (M-P-E) was used for *Candida utilis* cells for examination of turbidity change with the absorbance at 650 nm as the index, it was found to be reduced from 13.2 to 2.3 to confirm that the cells were recovered.

EXAMPLE 15

To a solution of 5 g of α-amino-ω-methoxy polyethylene glycol (average molecular weight 20,00) and 0.6 g of D-asparagine dissolved in 5 ml of water was added 5 g of a water-solule carbodiimide, and the reaction was carried out while pH is maintained at 4.5 for 20 hours. After extraction with chloroform, the extract was purified by ion exchange to obtain a polyethylene glycol-D-asparagine conjugate (P-E).

A solution of 1 g of the polyethylene glycol-D-asparagine (P-E) dissolved in 1.3 ml of water was adjusted to pH 8.0 with an aqueous ammonia and to this solution was added dropwise 0.6 ml of water containing 64 mg of ferrous chloride and 151 mg of ferric chloride. During the dropwise addition, pH was maintained at 8.0 to 8.5 with an aqueous ammonia, and the mixture was well stirred at room temperature. After sufficient dialysis of the reaction mixture against water, a magnetic material-Dasparagine conjugate (M-P-E) was obtained by lyophilization.

The magnetic material-D-asparagine conjugate (M-P-E) was found to contain 85% of the magnetic material and 5% of D-asparagine. The magnetic material-D-asparagine conjugate (M-P-E) was dispersed or dissolved as colloid in aqueous solutions and organic solvents such as benzene, toluene, chloroform, chlorinated hydrocarbons, and completely recovered from these solutions in 5 minutes in a magnetic field of 6000 Oersted (Oe). This was again dissolved as colloid in the reaction solution.

It was found that the magnetic material-D-asparagine conjugate (M-P-E) dissolved as colloid in the aqueous solution and organic solvents was not sedimented by centrifugation at 2,000×g, and its turbidity did not change for 24 to 60 hours in turbidity measurement at 600 nm. Thus the conjugate stably dispersed in an organic solvent. Also, in the aqueous solution, similar dispersion stability was observed. By electron microscope observation, the conjugate was found to consist of ultrafine particles with particle sizes of 10 to 40 nm.

The magnetic material-D-asparagine conjugate (M-P-E) had high affinity for asparaginase derived from *E. coli* and recovered asparaginase in an aqueous solution by magnetic separation.

EXAMPLE 16

A solution of 1.2 g of α,ω-dicarboxy polyethylene glycol (average molecular weight 4,000) dissolved in 0.8 ml of distilled water was adjusted to pH 8.0 with an aqueous ammonia and to this solution were added dropwise 0.4 ml of distilled water containing 120 mg of ferrous chloride and 51 mg of ferric chloride. During the dropwise addition, pH was maintained at 8.0 to 8.5 with an aqueous ammonia and the mixture was stirred well at 60° C. After the reaction mixture was dialyzed sufficiently against water, a magnetic material-polyethylene glycol conjugate (M-P) was obtained.

To 4 ml of a phosphate buffered solution (pH 5.0) containing 30 mg of RNA and 500 mg of the magnetic material-polyethylene glycol conjugate (M-P) was added 500 mg of a water-soluble carbodiimide and, after the reaction at 37° C. for 12 hours, 5 ml of water was added to the reaction mixture. The magnetic material-RNA conjugate (M-P-E) formed by maqnetic separation was thoroughly washed with water and then lyophilized to obtain a magnetic material-RNA conjugate (M-P-E).

The magnetic material-RNA conjugate (M-P-E) was found to contain 85% of the magnetic material and 3% of RNA. The magnetic material-RNA conjugate (M-P-E) was dispersed or dissolved as colloid in aqueous solutions and organic solvents such as benzene, toluene, chloroform, chlorinated hydrocarbons, and completely recovered from these solutions in 5 minutes in a magnetic field of 6,000 Oersted (Oe). This was again dissolved as colloid in the reaction solution.

It was found that the magnetic material-RNA conjugate (M-P-E) dissolved as colloid in the aqueous solution and organic solvents was not sedimented by centrifugation at 2,000×g, and its turbidity did not change for 24 to 60 hours in turbidity measurement at 600 nm. Thus the conjugate stably dispered in an organic solvent. Also, in the aqueous solution, similar dispersion stability was observed. By electron microscope observation, the conjugate was found to consist of ultra-fine particles with particle sizes of 10 to 40 nm.

The magnetic material-RNA conjugate (M-P-E) was bound to liposome, and recovered liposome from the cell extract by magnetic separation.

EXAMPLE 17

To 5 ml of an aqueous borate buffered solution (pH 9.5) containing an antitumor substance asparaginase (20 mg) obtained from *E. coli* was added 5 g of 2,4-bis(O-methoxypoly-ethylene glycol)-6-chloro-s-triazine, and the reaction was carried out at 25° C. for 90 minutes to obtain a polyethylene glycol-antitumor substance conjugate (P-E).

A solution of 1 g of the polyethylene glycol-antitumor substance conjugate (P-E) dissolved in 1.3 ml of water was adjusted to pH 8.0 with an aqueous ammonia and to this solution was added dropwise 0.6 ml of water containing 64 mg of ferrous chloride and 151 mg of ferric chloride. During the dropwise addition, pH was maintained at 8.0 to 8.5 with an aqueous ammonia, and the mixture was well stirred at room temperature. After sufficient dialysis of the reaction mixture against water, a magnetic material-antitumor substance conjugate (M-P-E) was obtained by lyophilization.

The magnetic material-antitumor substance conjugate (M-P-E) was found to contain 56% of the magnetic material and 25% of the antitumor substance. The magnetic material-antibody conjugate (M-P-E) was dispersed or dissolved as colloid in aqueous solutions (hydrophilic environments) and organic solvents (hydrophobic environments), and completely recovered from these solutions in 5 minutes in a magnetic field of 6,000 Oersted (Oe). This was again dissolved as colloid in the reaction solution. When the magnetic material-antitumor substance (M-P-E) was administered to the CBA mouse transplanted with *Gardonen lymphoma*, and a cobalt-samarium permanent magnet was placed against the afflicted site. As the result, as compared with Control group, significant elongation of living days was observed to confirm antitumor activity.

EXAMPLE 18

A solution of 1 g of α,ω-dimethoxycarbonyl pol glycol (average molecular weight 4,500) dissolved in 15 ml of water was adjusted to pH 8.0 with an aqueous ammonia and to this solution was added dropwise 2 ml of water containing 260 mg of ferrous chloride and 640 mg of ferric chloride. During the dropwise addition, pH was maintained at 8.0 to 9.0 with an aqueous ammonia, and the mixture was well stirred. After sufficient dialysis of the reaction mixture against water, a magnetic material-polyethylene glycol conjugate (M-P) was obtained by lyophilization.

The conjugate (M-P) was dissolved or dipersed as colloid in aqueous solutions and benzene, and completely recovered from these solutions in 5 minutes in a magnetic field of 5,000 (Oe). This was dissolved again as colloid in the solution. It was found that the magnetic material-polyethylene glycol conjugate (M-P) dissolved as colloid in the aqueous solution and benzene was not sedimented by centrifugation at 5,000×g, and its turbidity did not change for 24 to 60 hours in turbidity measurement at 600 nm. Thus the conjugate stably dispersed in an organic solvent. The conjugate contained 40% of the magnetic material, and by electron microscope observation, the conjugate was found to consist of ultra-fine particles with particle sizes of 10 to 40 nm.

Other than benzene, in solvents in which polyethylene glycol can be dissolved such as toluene chloroform, trichloroethylene, pyridine, acetone, dioxane, methanol, ethanol, dimethylformamide, dimethyl sulfoxide, etc., the magnetic material-polyethylene glycol conjugate (M-P) exhibited iimilar properties.

To the carboxyl groups of the magnetic material-polyethylene glycol conjugate (M-P) was bound N-hydroxysuccinimide in dioxane according to a conventional method to synthesize an activated magnetic material-polyethylene glycol con0ugate (M-P) (activated magnetic material modifier).

(a - 1) An amount of 75 mg of the above activated magnetic material-polyethylene glycol conjugate (M-P) was added to 4 ml of a phosphate buffered solution (pH 7.0) containing 5 mg of lipase obtained from *Pseudomonas fraqi* 22-39B cells and, after the reaction at 37° C. for 90 minutes, the product was purified to obtain a magnetic material-lipase conjugate (M-P-E) having similar dissolution stability and magnetic separation characteristics as the magnetic material-polyethylene glycol conjugate (M-P). Further, the magnetic material-lipase conjugate (M-P-E) exhibited a hydrolysis activity of olive oil of 1,500 units/mg protein and a synthetic activity of lauryl laurate of 10 μmol/min./mg protein in benzene. This activity was not lost even when the conjugate was recovered magnetically from the solution and dissolved again in the solution.

(a - 2) In place of lipase, subtilicin derived from *Bacillus subtilis*, catalase derived from bovine liver and esterase were modified by use of the activated, magnetic polyethylene glycol conjugate (M-P), whereby dissolution stability and magnetic separation characteristics similar to the conjugate could be given.

(a - 3) Even by use of anti-p-nitrophenol antibody in place of lipase in (a - 1), a magnetic material-antibody conjugate (M-P-E) having dissolution stability and magnetic separation characteristics similar to the magnetic material-polythylene glycol conjugate (M-P) was obtained. By use of this, p-nitrophenol in benzene could be magnetically separated and recovered.

(b - 1) Also by use of those having molecular weights 750 (3 g), 2000 (1.5 g), 20,000 (0.7 g), 200,000 (0.5 g) in place of the α,ω-dimethoxycarbonyl polyethylene glycol with molecular weight of 4,500, magnetic material-polyethylene glycol conjugates (M-P) having similar properties were obtained.

(b - 2) Also by use of α-methoxycarbonyl-ω-methoxypolyethylene glycol (average molecular weight 4,500) in place of the α,ω-dimethoxycarbonyl polyethylene glycol, magnetic material-polyethylene glycol conjugates having similar properties were obtained.

(b - 3) Also by use of a polyethylene glycol or a monomethoxypolyethylene glycol (average molecular weight 5,000), α,ω-diaminopropyl polyethylene glycol (average molecular weight 4,500), α-aminopropyl-ω-methoxy polyethylene glycol (averaqe molecular weight 4,500) in place of the α,ω-dimethoxy cabonyl polyethylene glycol, magnetic material-polyethylene glycol conjugates (M-P) having similar properties were obtained. Activated magnetic material-polyethylene glycol conjugates (M-P) were synthesized by binding cyanuric chloride to the hydroxyl groups or amino groups of the conjugates according to a conventional method.

EXAMPLE 19

A solution of 1 g of α,ω-dimethozycarbonyl polyethylene glycol (average molecular weight 4,500) dissolved in 15 ml of water was adjusted to pH 8.0 with an aqueous ammonia and to this solution was added dropwise 2 of distilled water containing 200 mg of ferrous chloride, 40 mg of cobalt chloride and 640 mg of ferric chloride. During the dropwise addition, pH was maintained at 8.0 to 9.0 with an aqueous ammonia, and the mixture was well stirred. After sufficient dialysis of the reaction mixture against water, a magnetic material-polyethylene glycol conjugate (M-P) was obtained by lyophilization. This conjugate exhibited dissolution stability and magnetic separation characteristics similar to the conjugate obtained in Example 18, and could be used as a chemical modifier.

We claim:

1. A conjugate, comprising a magnetic material and a physiologically active substance bound to each other through a polyethyelen glycol derivative.

2. A conjugate, comprising a magnetic material and a polyethylene glycol derivative bound to each other.

3. The conjugate of claim 2, wherein the polyethylene glycol derivative has a molecular weight of 500 to 200,00.

4. The conjugate according to claim 2, wherein the polyethylene glycol derivative is α, ω-di-carboxy polyethylene glycol or α,ω-dimethozycarbonyl polyethylene glycol having a molecular weight of 500 to 200,00 and the magnetic material is formed from ferrous chloride and ferric chloride.

5. The conjugate according to claim 4, further comprising enzyme bound to the conjugate.

6. The conjugate according to claim 1, wherein the polyethylene glycol derivative has a molecular weight of 500 to 200,000.

7. The conjugate according to claim 1, wherein the polyethylene glycol derivative has at least one selected from the group consisiting of hydroxyl group, carboxyl group, methoxycarbonyl group, amide group, amino group and mthoxy group at termainal ends.

8. The conjugate according to claim 1, wherein the polyethylene glycol derivative has carboxyl group or methoxycarbonyl group at terminal ends.

9. The conjugate according to claim 1, wherein the magnetic material is a transition metal or its ion, its oxide or a compound of these with other elements.

10. The conjugate according to claim 1, wherein the magnetic material is formed from ferrous chloride or ferric chloride.

11. The conjugate according to claim 1, wherein the magnetic material is ferrite or magnetite.

12. The conjugate according to claim 1, wherein the magnetic material is erbium oxide or dysprosium chloride.

13. The conjugate according to claim 1, wherein the physiologically active aubstance is an enzyme, a protein, an antibody, an antigen, a polysaccharide, a nucleic acid, a lipid, an amino acid, a co-enzyme, ATP, ADP, heme, riboflavin, a hormone, a vitamin, a ligand, an antibiotic, an antitumor substance, or a chloroplast, a mitochrondrion, a virus, or a protein constituting Bacterial cell.

14. The conjugate of claim 13, wherein the polyethylene glycol derivative has at least one group selected from the group consisting of hydroxyl group, carboxyl group, methoxycarbonyl group, amide group, amino group and methoxy group, at terminal ends.

15. The conjugate according to claim 14, wherein the polyethylene glycol derivative has carobyxl group or methoxycarbonyl group at terminal ends.

16. The conjugate according to claim 14, wherein the magnetic material is a transition metal or its ion, its oxide or a compound of these with other elements.

17. The conjugate according to claim 14, wherein the magnetic material is formed form ferrous chloride or ferric chloride.

18. The conjugate according to claim 14, wherein the magnetic material is ferrite or magnetite.

19. The conjugate according to claim 14, wherein the magnetic material is erbium oxide or dysprosium chloride.

20. The conjugate of claim 14, wherein the polyethylene glycol derivative has a molecular weight of 500 to 200,000.

21. The conjugate according to claim 1, wherein the physiologically active substance is an enzyme, a protein, an antibody or an antigen.

22. The conjugate according to claim 1, wherein the physiologically active substance is an enzyme.

23. The conjugate according to claim 1, wherein the physiologically active substance is lipase.

24. The conjugate of claim 14 wherein the polyethylene glycol derivative has a molecular weight of 500 to 200,000.

* * * * *